United States Patent [19]

Huang et al.

[11] 4,086,142

[45] Apr. 25, 1978

[54] DECARBOXYLATION OF ENDOGENOUS SERUM GLUTAMATE IN TRANSAMINASE ASSAYS

[75] Inventors: Charles Y. Huang, Potomac, Md.; William S. Stavropoulos, Carmel, Ind.

[73] Assignee: The Dow Chemical Company, Midland, Mich.

[21] Appl. No.: 747,860

[22] Filed: Dec. 6, 1976

[51] Int. Cl.² ............................................. G01N 31/14
[52] U.S. Cl. ............................................... 195/103.5 R
[58] Field of Search .................................. 195/103.5 R

[56] References Cited

U.S. PATENT DOCUMENTS 3,992,158  11/1976  Przybylowicz et al. ......... 23/253 TP
4,024,021  5/1977   Stavropoulos et al. ......... 195/103.5 R

OTHER PUBLICATIONS

Bergmeyer, "Method of Enzymatic Analysis", Academic Press, Inc. New York and London, (1974) pp. 1662–1668.

Primary Examiner—Alvin E. Tanenholtz
Assistant Examiner—C. A. Fan
Attorney, Agent, or Firm—James W. Ambrosius

[57] ABSTRACT

A spectrophotometric method for carrying out transaminase determinations of biological fluids wherein endogenous glutamate in a biological fluid is decarboxylated prior to transaminase determinations with bacterial glutamic acid decarboxylase.

6 Claims, 2 Drawing Figures

DECARBOXYLATION OF ENDOGENOUS SERUM GLUTAMATE IN TRANSAMINASE ASSAYS

BACKGROUND OF THE INVENTION

Spectrophotometric determinations of transaminases (aminotransferases) present in biological fluids have been used as an aid in the diagnosis of myocardial infarction and the necrosis of hepatic cells. The enzymes of primary significance are glutamic oxalacetic transaminase, hereinafter called GOT, and glutamic pyruvic transaminase, hereafter called GPT. These enzymes catalyze the following reactions.

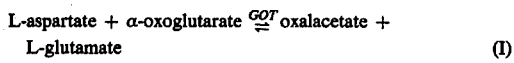

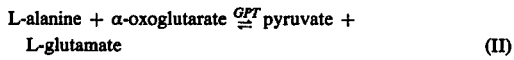

Various colorimetric methods for the determination of transaminases have been described. See Reitman, et al., *Amer. J. Clin. Pathol.* 28, 56 (1956) and Babson, et al., *Clin. Chim. Acta* 7, 199 (1962). Disadvantages associated with these methods include non-linear activity curves and long overall reaction times.

In 1970, Lippi, et al., *Clin. Chim. Acta.* 28, 431, described a glutamate-linked approach which utilized glutamate dehydrogenase and phenazonium methosulfate to generate a formazon dye. This method was later improved by Stavropoulos and Acuff, U.S. Pat. No. 4,024,021. In both methods, however, the presence of endogenous serum glutamate can result in falsely elevated transaminase activity.

In measuring serum GOT and serum GPT activity by the procedure of Lippi, et al. and as improved by Stavropoulos, et al., the endogenous glutamate present in the serum is converted to the final product, a formazon dye. This shows up as an initial "burst" in the product formation curve. Although the activity can be calculated from the linear portion of the product formation curve beyond the burst, if the serum level of glutamate is high the burst may be greater than two absorbance units under the conditions described hereinbelow, which makes accurate measurements difficult to obtain. In addition, the burst would result in falsely elevated activity in an end-point assay method where the reaction is stopped after a set reaction time.

SUMMARY OF THE INVENTION

The present invention is directed to an improved method of carrying out glutamate-linked transaminase determinations where glutamate is analyzed and used as an indication of transaminase activity. The improved procedure overcomes the effect of endogenous serum glutamate and provides accurate results and high precision in an end-point assay method.

In order to overcome the interference from endogenous serum glutamate, the serum sample is first treated with a microbial glutamic acid decarboxylase, particularly a bacterial glutamic acid decarboxylase, hereafter GDC at a pH of about 4 or 5 prior to GOT or GPT assay. The reaction catalyzed by GDC is as follows:

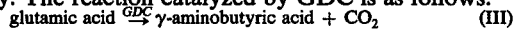

Since microbial GDC, usually obtained from *Escherichia coli* (*E. coli*), *Clostridium perfringens*, or from other suitable sources has a pH optimum of about 4 or 5 and is inactive at neutral or alkaline pH, this enzyme does not interfere with serum GOT and GPT assay methods which usually are performed at a pH of between 7 and 9. This pre-treatment step eliminates endogenous glutamate in the serum, results in a linear product formation curve and makes possible the accurate assay of serum GOT and GPT by either a continuous or end-point procedure. Furthermore, since serum GOT and GPT assays are generally carried out at about 37° C. the reagents are pre-warmed to the desired temperature. The decarboxylation reaction therefore can take place during this preincubation period and will not appreciably change the overall time for performing the assays. Correlation of GOT and GPT activities measured using this improved method and other established methods is very good (see Examples 3 and 4 following).

It is seen therefore that the present invention has two main features. First, the endogenous serum glutamate is eliminated by pre-treatment with the enzyme GDC. Second, the difference in pH optima of microbial GDC and GOT or GPT is utilized so that the different reactions do not interfere with each other.

DESCRIPTION OF DRAWINGS

Referring now to the drawings.

DETAILED DESCRIPTION OF THE INVENTION

Figure 1:
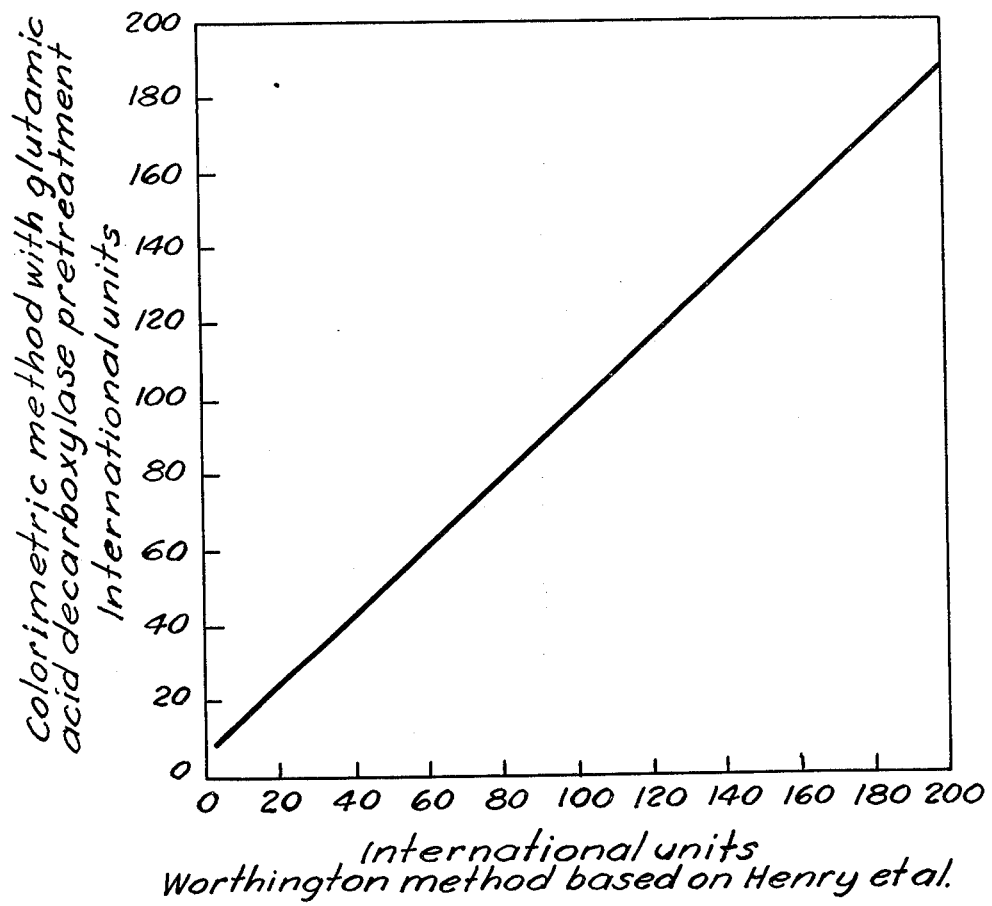
FIG. 1 shows correlation data comparing the colorimetric method of serum GPT determination using pretreatment with glutamic acid decarboxylase as described herein with a commercially available method accepted in the art.

The present invention is intended as an improvement in methods useful for transaminase determination of biological fluids which use glutamate generated by reactions I and II above to assay for activities of GOT and GPT. Thus, the present invention may be used as an improvement to and in conjunction with the process described either by Lippi et al. or Stavropoulos et al. referenced hereinbefore. As used herein, the term biological fluid refers to any biological fluid in which GOT or GPT determinations may be carried out such as serum, plasma, lymphatic fluid, tissue extracts, enzyme preparations or the like.

Purification of bacterial GDC intended for use in the present invention is necessary since commercial enzyme preparations contain unwanted impurities, such as GOT, GPT, and glycerol dehydrogenase, any of which could introduce side reactions into the system and result in high reagent blanks. It was found commercially available GDC from *E. coli* could be readily purified in the laboratory by column chromatography. The purification of GDC from *E. coli* has been described by Strausbouch, et al., *Biochem. Biophys. Res. Comm.* 28, 525 (1967). The purification of GDC from *Clostridium perfringens* has been shown in Cizzani, et al., *Biochem. J.* 118, 135 (1970).

As used herein, one international unit of enzyme activity is the amount sufficient to convert one micromole of glutamic acid per minute at 37° C at a pH of about 4–5. It has been found that about 0.4 international units of purified GDC are sufficient to decarboxylate the endogenous glutamate present in 0.1 ml of human serum in about 7 to 10 minutes at 37° C at a pH of about 5.

In carrying out the decarboxylation reaction, in general, higher concentrations of enzyme require shorter incubation times. Conversely lower concentrations of GDC require longer incubation times. Most transaminase determinations are carried out at a temperature of 37° C and the time required to bring the reagent from room temperature to the desired temperature is utilized to perform the decarboxylation. Lower temperatures are also operable, but the incubation time must be increased to achieve complete decarboxylation prior to analysis for serum GOT/GPT. Thus, the exact concentration of GDC required to achieve decarboxylation will depend upon such factors as, for example, the source of the enzyme, temperature, incubation time, pH, and the amount of serum used. An effective amount of GDC, therefore, is defined as the amount of GDC required to completely decarboxylate the endogenous glutamate present in a unit amount of biological fluid within 10 to 20 minutes. Although excess GDC generally has no significant effects on transaminase determination, as a practical matter a maximum of about 3 or 4 international units of GDC is used to pretreat 0.1 ml of serum.

As noted above, the present invention may be practiced in combination with the procedure described by Stavropoulos et al. This combined procedure was found to give a very convenient and practical test for the assay of GOT and GPT in serum. The improved procedure of the present invention is described in Example 1 below, but this example is not to be construed as a limitation upon the scope of the invention.

EXAMPLE 1

Step 1: Decarboxylation of Serum Glutamate at pH 5

A 0.1 ml serum sample is pipetted into 1.0 ml of an aqueous mixture containing 3 mmoles of nicotinamide adenine dinuclotide, 0.2 mmoles of ethylenediamine tetracetic acid, 0.75 mg of 2-(p-iodophenyl)-3-(p-nitrophenyl)-5-phenyl tetrazolium chloride, 1 international unit of GDC from *E. coli* (ATCC 11246), 15 mg of mannitol, 5 $\mu$moles of adenosine-5'-diphosphate, 5.2 $\mu$moles of acetic acid acetate buffer, (pH 4.6), and 75 $\mu$moles of L-aspartate (for serum GOT assay) or 130 $\mu$moles of L-alanine (for serum GPT assay). The mixture is then allowed to reach 37° C in a constant heat source such as a heating block or water bath. The serum glutamate is decarboxylated during this incubation time (generally about 10 minutes). The final pH of the pretreatment mixture is about 4.9–5.3.

Step 2: Serum GOT/GPT assay

Serum GOT/GPT assay is started by the addition of 0.2 ml of a starting mixture having a pH of 8.6 and containing 60 international units of glutamate dehydrogenase, 0.24 international units of diaphorase 7.5 $\mu$moles of $\alpha$-oxoglutarate, and 37.5 $\mu$moles of potassium pyrophosphate. The final pH of the serum GOT/GPT reaction is 8.2–8.4. The absorbance change at 500 nanometers due to the formation of the reduced INT chromophor can be followed continuously on a spectophotometer. Alternatively, the reaction may be stopped after 10 minutes by the addition of 3 ml of 0.1 M hydrochloric acid and the absorbance read at 500 nanometers with a colorimeter. A reagent blank is prepared by adding 0.1 ml of water in place of 0.1 ml of serum.

A standard is prepared by adding 0.2 ml of the starting mixture to the 1.0 ml incubation mixture of step 1. This is followed by the addition of 0.1 ml of glutamate standard solution containing 0.05 $\mu$moles of glutamic acid. This reaction mixture is incubated for a time equivalent to that used for the serum test sample.

The following example shows one method of processing the GDC prior to use in the method of this invention. Enzyme purified by this method has been shown to give satisfactory results when used in the procedure of Example 1 above.

EXAMPLE 2

Purification Procedure for Glutamic Decarboxylation From *E. Coli*

1. 160 mg of crude GDC containing about 3.5 units/mg was dissolved in 4 ml of 20 mM acetate buffer, pH 5.5.

2. The GDC solution was introduced into a 1.5 × 18 cm DEAE-cellulose column pre-equilibrated with 20 mM acetate buffer, pH 5.5. The column was washed with 150 ml of the same buffer and then eluted with a 400 ml linear gradient of 0–0.5 M potassium chloride in the same buffer. Six ml fractions were collected.

3. The fractions were assayed for GDC activity and fractions which had specific activities greater than 50 units (at 37° C, pH 5.5) per mg were pooled and stored at 4° C.

EXAMPLE 3

Using the general method outlined in Example 1 above 39 samples of serum were assayed for GPT activity. The serum samples were also assayed for GPT activity using the commercially available reagent and procedure supplied by Worthington Diagnostics. This method is based upon the procedure of Henry, et al., *Amer. J. Clin. Path.* 34, 381 (1960). The data is shown in FIG. 1.

Linear regression analysis of the data obtained with the Worthington method and the method that is the subject of the present invention yielded a correlation coefficient of 0.998.

EXAMPLE 4

Figure 2:
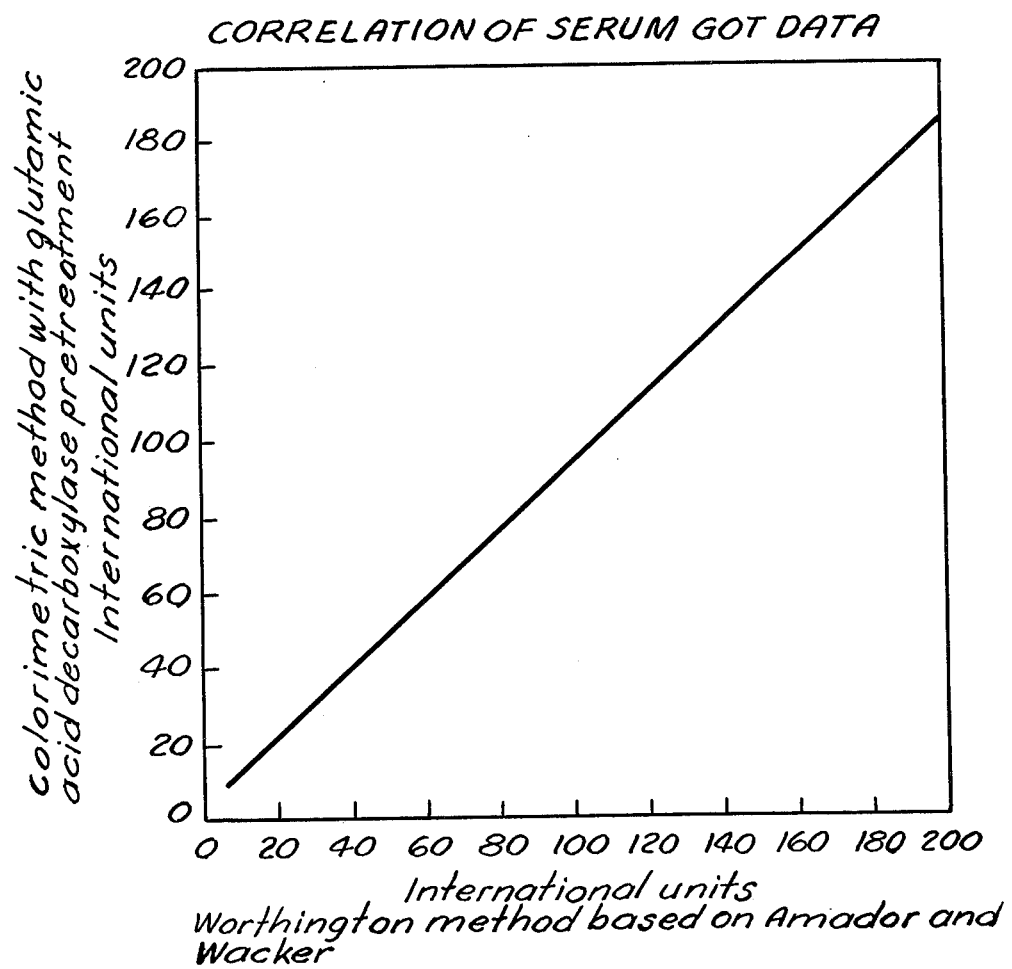
FIG. 2 contains similar data for the serum GOT determinations.

In a similar manner as described in Example 3 above, 38 serum samples were assayed for GOT activity. The reference method and reagents were a commercially available kit from Worthington Diagnostics based upon the procedure of Amador and Wacker, *Clin, Chem.* 8, 343 (1962). The data is graphed in FIG. 2.

Linear regression analysis of the data yielded a correlation coefficient of 0.981.

We claim:

1. In a colorimetric method for the determination of glutamic transaminase activity in biological fluids having endogenous glutamate present wherein the transaminase activity is determined by an assay for the amount of glutamate generated by an amino acid and $\alpha$-oxoglutarate in the presence of the glutamic transaminase by measuring the absorbance of a color reaction product the improvement which comprises incubating prior to glutamate assay the biological fluid with an effective glutamate decarboxylating amount of a microbial glutamic acid decarboxylase at a pH of from about 4 to about 5 for a time sufficient to decarboxylate the endogenous glutamate in the biological fluid.

2. The method of claim 1 wherein the glutamic acid decarboxylase is inactive at neutral or alkaline pH.

3. The method of claim 1 wherein the microbial glutamic acid decarboxylase is obtained from Escherichia coli.

4. The method of claim 4 wherein the biological fluid is serum.

5. The method of claim 1 wherein the change in absorbance of light is measured on a colorimeter.

6. The method of claim 3 wherein the amount of microbial glutamic acid decarboxylase present is from 0.4 to 4 international units per 100 microliters of biological fluid.

* * * * *

UNITED STATES PATENT AND TRADEMARK OFFICE
CERTIFICATE OF CORRECTION

PATENT NO. : 4,086,142
DATED : April 25, 1978
INVENTOR(S) : Charles Y. Huang and William S. Stavropoulos It is certified that error appears in the above-identified patent and that said Letters Patent are hereby corrected as shown below:

Column 5, line 6 "claim 4" should read -- claim 1 --.

Signed and Sealed this

Nineteenth Day of September 1978

[SEAL]

Attest:

RUTH C. MASON
*Attesting Officer*

DONALD W. BANNER
*Commissioner of Patents and Trademarks*